United States Patent
Huo et al.

(10) Patent No.: US 11,921,099 B2
(45) Date of Patent: Mar. 5, 2024

(54) METHOD FOR QUANTITATIVELY ANALYZING RESERVOIR FORMATION OF ULTRA-DEEP EVAPORITE-DOLOMITE SYMBIOTIC SYSTEM

(71) Applicant: SOUTHWEST PETROLEUM UNIVERSITY, Chengdu (CN)

(72) Inventors: Fei Huo, Chengdu (CN); Xingzhi Wang, Chengdu (CN); Huaguo Wen, Chengdu (CN); Huiwen Huang, Chengdu (CN); Yunbo Ruan, Chengdu (CN); Liang Li, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 18/362,045

(22) Filed: Jul. 31, 2023

(65) Prior Publication Data

US 2024/0019414 A1  Jan. 18, 2024

(51) Int. Cl.
*G01N 33/24* (2006.01)
*G01N 23/20* (2018.01)
*G01N 23/2254* (2018.01)
*H01J 49/10* (2006.01)

(52) U.S. Cl.
CPC ............. *G01N 33/24* (2013.01); *G01N 23/20* (2013.01); *G01N 23/2254* (2013.01); *H01J 49/105* (2013.01)

(58) Field of Classification Search
CPC .... G01N 33/24; G01N 23/20; G01N 23/2254; H01J 49/105
See application file for complete search history.

(56) References Cited

U.S. PATENT DOCUMENTS

2021/0270130 A1    9/2021  Lu et al.

FOREIGN PATENT DOCUMENTS

| CN | 104655821 A | * | 5/2015 |
| CN | 104655821 A | | 5/2015 |
| CN | 105137033 A | * | 12/2015 |
| CN | 105137033 A | | 12/2015 |

(Continued)

OTHER PUBLICATIONS

Huaguo Wen et al., "Advances and Prospects of Dolostone-evaporite Paragenesis System", Acta Sedimentologica Sinica, Dec. 2021, vol. 39, No. 6, pp. 1321-1343.

(Continued)

*Primary Examiner* — Michael J Dalbo
*Assistant Examiner* — Kaleria Knox

(57) ABSTRACT

A method for quantitatively analyzing the reservoir formation of an ultra-deep evaporite-dolomite paragenesis system is performed as follows. A typical drilling core containing the evaporite-dolomite paragenesis system and a field section are observed. The logging data is subjected to single-factor analysis to determine the planar distribution regularity of the ultra-deep evaporite and the dolomite, and the analysis of sedimentary combination pattern and development evolution regularity is performed. The diagenetic system is determined, and the reservoir formation of the evaporite-dolomite paragenesis system is analyzed. Based on the above technical solutions, the property, the evolution path and the reservoir formation of sedimentation-diagenesis fluids in the evaporite-dolomite paragenesis system can be clarified.

7 Claims, 2 Drawing Sheets

(56) References Cited

FOREIGN PATENT DOCUMENTS

| | | | | | |
|---|---|---|---|---|---|
| CN | 107015290 | A | * | 8/2017 | ............ G01N 33/24 |
| CN | 111983189 | A | * | 11/2020 | ............ G01N 33/24 |
| CN | 111983189 | A | | 11/2020 | |
| WO | 2016130945 | A1 | | 8/2016 | |

OTHER PUBLICATIONS

Jianfeng Zheng et al., "Main Controlling Factors and Characteristics of Cambrian Dolomite Reservoirs Related to Evaporite in Tarim Basin", Acta Sedimentologica Sinica, Feb. 2013, vol. 31, No. 1, pp. 89-98.

Bin Bai et al., "The Effect of Supergene Karstification and Its Significance of the Gypsum-salt-Carbonate Paragenesis in Majiagou Formation of Ordos Basin", Journal of Yangtze University(Natural Science Edition) ,2017, vol. 14, No. 3, pp. 7-12.

* cited by examiner

METHOD FOR QUANTITATIVELY ANALYZING RESERVOIR FORMATION OF ULTRA-DEEP EVAPORITE-DOLOMITE SYMBIOTIC SYSTEM

CROSS-REFERENCE TO RELATED APPLICATIONS

This application claims the benefit of priority from Chinese Patent Application No. 202210937615.1, filed on Aug. 5, 2022. The content of the aforementioned application, including any intervening amendments thereto, is incorporated herein by reference in its entirety.

TECHNICAL FIELD

This application relates to oil and gas extraction, and more particularly to a method for quantitatively analyzing reservoir formation of an ultra-deep evaporite-dolomite paragenesis system.

BACKGROUND

The distribution area of carbonate rocks accounts for 20% of the total area of the global sedimentary rocks, while about 60% of the global oil and gas production is from the carbonate rocks (Ma Feng, Yang Liuming, Gu Jiayu, Chen Xi, Zhao Zhe, Jin Yinnan, Gao Li. The Summary on Exploration of the Dolomite Oilfields in the World[J]. Acta Sedimentologica Sinica, 2011, 29(5): 1010-1021). The diversity of the carbonate sedimentary system and the complex diagenesis lead to diverse reservoir types, which can be lithologically classified into dolomite reservoir and limestone reservoir (Zhu Xiaomin, 2008). According to the data statistics of 226 large-medium and giant carbonate oil and gas reservoirs worldwide (accounting for 90% of the global carbonate oil and gas reserves), half of the oil and gas is held in dolomites. Compared with other types of oil and gas reservoir rocks, the dolomites have better porosity, and are considered as ideal carriers for holding oil and gas (Warren, 2000; Ma Yongsheng et al., 2019). With the discovery and exploitation of multiple large and giant gas fields, such as Anyue, Moxi, Puguang, Longgang and Yuanba, the proved reserves of the Sichuan Basin have reached $4.77 \times 10^{12}$ m$^3$ (He Dengfa et al., 2019). Most of the reserves are dolomite reservoirs, and a very small proportion of them are located at the limestone reservoirs (Ma Yongsheng et al., 2010). Similarly, in the Tarim Basin and the Ordos Basin, the dolomite also serves as the dominant "sweet spot" for oil and gas development, and is considered as the focus area for improving reserve and production. Regarding the current research focus "ultra-deep evaporite and dolomite", there are still many problems to be overcome.

In the carbonate strata, all the high-quality oil and gas reservoirs often experienced dolomitization, such that most of the oil and gas are hosted in the dolomite reservoirs of the carbonate. It has been found that in the deep-ultra deep carbonate formation of the Sichuan Basin, the dolomite generally forms a paragenesis system with the evaporite, and the evaporite exists either on the top of or underneath the dolomite. The diagenesis mechanism between the evaporite and the dolomite is particularly important, and the quantitative analysis of the diagenesis mechanism would significantly promote the exploration of paragenesis of the evaporite and dolomite. However, less attention has been paid to the diagenesis of the evaporite and dolomite, and the existing qualitative researches are not sufficient to support the in-depth study related to the evaporite and dolomite.

The dissolution of evaporite will release $Ca^{2+}$ and $SO_4^{2-}$, leading to an increased concentration of $Ca^{2+}$ and $SO_4^{2-}$ in the formation fluids. The role of $SO_4^{2-}$ in controlling the dissolution-precipitation equilibrium of the dolomite still remains highly controversial. It has been suggested that the evaporite dissolution can facilitate the dissolution of the dolomite at a low temperature, while at a high temperature, the formed mineral precipitate will consume $SO_4^{2-}$, thus weakening its effect of promoting the dolomite dissolution (Huang Sijing et al., 1996, 2012). It has also been proposed that the $SO_4^{2-}$ released from the evaporite dissolution would form a complex with $Mg^{2+}$ at high temperature through ion-pairing effect to consume Mg 2+, thus accelerating the dissolution of the dolomite (Song Huanrong et al., 1993; Wang et al., 2016; Ding Qian et al., 2017; He Zhiliang et al., 2021). Moreover, in terms of the genetic mechanism of the dolomite, the $SO_4^{2-}$ has been demonstrated to show an inhibition effect (Baker and Kastner, 1981; Kastner, 1984) or a catalysis effect (Morse et al., 2007; Sanchez-Roma n et al., 2009) on the formation of the dolomite, but the mechanism still remains unclear.

The Rb—Sr, Sm—Nd and U—Pb isotope dilution of authigenic calcite has been commonly adopted to analyze the timing of the paleo-fluid activities (Moorbath et al., 1987; Smith et al., 1994; Barker et al., 2009; Gorokhov et al., 2016). However, this method has complex pretreatment, low accuracy, and high requirements for the content and ratio of isotopes of dating samples (Barker et al., 2009; Woodhead and Pickering, 2012). Additionally, such method requires the dating samples to be products of fluid activities of the same stage, and different samples need to vary in the isotope ratios ($^{87}Rb/^{86}Sr$, $^{147}Sm/^{144}Nd$, $^{238}U/^{206}Pb$) to obtain the isochron age. However, in the researches on hydrothermal fluids in the carbonate, due to the multi-stage fluid activities in the basins, the calcite dating samples are often products of multi-stage fluid activities, resulting in a poor application effect (Jin Zhijun et al., 2013).

Some researches have also been conducted on fracture veins to reconstruct the information of fluid properties and activity stage (Sibson, 1987; Qiu Nansheng et al., 2000; Becker et al., 2010; Capezzuoli et al., 2018). Traditionally, the whole-rock geochemical assay is often used to analyze the trace elements (including rare earth elements), and the C—O and Sr isotope composition of the veins generated in fluid activities. Since the trace elements (including rare earth elements) are susceptible to the hydrological change of sedimentary environment, the veins formed in the multi-stage fluid activities will vary in the distribution pattern of rare earth elements (Piper et al., 2015; Guo Xiaowen et al., 2020). The C—O and Sr isotope composition may also be used to determine characteristics and origin of the fluid and reveal the source region of the fluid in combination with the previous indicators and illustration (Holmden, 1995; Roskowski et al., 2010; Slater and Smith, 2012). Most of the basins in China are superimposed basins (Jin Zhijun, 2005; Pang et al., 2010), which are characterized by multi-stage sedimentation-diagenesis and hydrocarbon generation and expulsion after experiencing multiple complex tectonic activities. In this case, multi-stage paleo-fluid activities may be recorded in the same vein, and thus the whole-rock analysis still has some limitations for failing to accurately reveal the characteristics and stages of the multi-stage fluid activity recorded in the same vein.

SUMMARY

An object of this application is to provide a method for quantitatively analyzing the reservoir formation of an ultra-deep evaporite-dolomite paragenesis system, by which the formation mechanism of the diagenetic fluid between ultra-deep evaporite and dolomite in the Sichuan Basin may be quantitatively analyzed, providing a strong technical support for prediction, exploration and development of oil and gas reservoirs, especially those in the Sichuan Basin.

The technical solutions of this application are described as follows.

This application provides a method for quantitatively analyzing reservoir formation of an ultra-deep evaporite-dolomite paragenesis system, comprising:

step (1) selecting a typical drilled well to observe a core characteristic of a development section of the ultra-deep evaporite-dolomite paragenesis system; and describing and determining a vertical development characteristic of the ultra-deep evaporite-dolomite paragenesis system to determine a development and distribution regularity of the ultra-deep evaporite-dolomite paragenesis system;

step (2) selecting a typical field outcrop section; obtaining field outcrop data of the ultra-deep evaporite-dolomite paragenesis system through combination of typical section measurement and key section observation; and collecting a paragenetic evaporite-dolomite sample laboratory research;

step (3) systematically collecting logging data of an evaporite stratum to establish a lithology identification plate; recording a thickness of an evaporite and marking a planar boundary of the evaporite; establishing a thickness isoline map of the evaporite and a dolomite in a layered manner; and identifying a planar distribution pattern of individual components of the ultra-deep evaporite-dolomite paragenesis system;

step (4) based on the development and distribution regularity obtained in step (1) and the field outcrop data obtained in step (2), analyzing and determine a combination pattern of the ultra-deep evaporite-dolomite paragenesis system to investigate an evolution pattern and a planar distribution characteristic of a combination of different substances in the ultra-deep evaporite-dolomite paragenesis system;

step (5) with a salt inclusion as an initial fluid, inversing a property of a diagenetic fluid by measuring race and rare-earth elements, C, O, Sr and Mg isotopes and clumped isotopes of the dolomite; performing a simulation experiment of a water-rock interaction during a main evolution phase according to petrological characteristics of the ultra-deep evaporite-dolomite paragenesis system in combination with burial history; and with strata water in a current drilled well as an end point, systematically inversing temperature and pressure characteristics and water-rock interaction process of a diagenetic system to obtain characteristics of a diagenetic field and a transformation force and an evolution process of the diagenetic field, so as to determine the diagenetic system; and step (6) based on the planar distribution pattern obtained in step (3) and the evolution pattern and the planar distribution characteristic obtained in step (4), identifying a type of a reservoir, and analyzing development characteristic and regularity of the reservoir; based on the diagenetic system determined in step (5), analyzing an evolution and formation process of the reservoir and a reservoir formation mechanism to establish a reservoir development model; and quantitatively analyzing the reservoir formation of the ultra-deep evaporite-dolomite paragenesis system based on the reservoir development model.

In some embodiments, in step (5), the Mg isotope is measured through steps of:
(a) based on petrographic section analysis, performing micro-area sampling according to carbonate composition;
(b) dissolving a powder sample with a 0.5 N acetic acid solution to obtain a sample solution;
(c) purifying Mg from the sample solution with an ion exchange column; and
(d) measuring a Mg isotope ratio by using a Multi-Collector Inductively Coupled Plasma Mass Spectrometry (MC-ICP-MS) solution method.

In some embodiments, microstructure observation and mineral composition identification of the dolomite are performed by using a polarized optical microscope.

In some embodiments, ultramicroscopic mineral morphology and structure of the evaporite and the dolomite are observed under a scanning electron microscope (SEM).

In some embodiments, mineral structure characteristics of the evaporite and dolomite, variation of an order degree of the dolomite and variation of Fe and Mn in crystals of the dolomite are identified by X-ray diffraction (XRD).

In some embodiments, obtaining of a micro-area morphological image of a survey area and quantitative analysis of components and constituent elements of the survey area are performed by using an electron probe microanalyzer (EPMA).

In some embodiments, mineral classification of the evaporite and dolomite and a microenvironmental change of the diagenetic fluid are analyzed by cathodoluminescence (CL).

Compared with the prior art, this application has the following beneficial effects.

(1) This application is characterized by accurate and complete analysis, which can clarify the characteristic, evolution path and reservoir formation of sedimentation-diagenesis fluids in the evaporite-dolomite paragenesis system, thereby providing theoretical support and analysis guidance for the prediction of favorable reservoir facies.

(2) Based on the solutions in this application, it is possible to determine the properties and stage of dolomitized fluids in different types of evaporite-dolomite paragenesis systems, identify different dolomitization processes, clarify the evolution path and reservoir formation of dolomitized fluids, and establish a genetic model of dolomite in different paragenesis systems.

(3) Based on the solutions in this application, it is possible to explain the mechanism of dissolution modification of reservoir space in evaporite-dolomite paragenesis systems by different types of diagenetic fluids, and to quantitatively analyze the mechanism of the dissolution porosity increase of evaporite-dolomite paragenesis systems under ultra-deep burial conditions.

(4) Based on the solutions in this application, it is possible to clarify the reservoir characteristic, reservoir type, diagenetic evolution process and reservoir formation mechanism of the evaporite-dolomite paragenesis system, thereby facilitating establishing the formation model of high-quality reservoirs formed during the sedimentation-diagenesis evolution process of evaporite-dolomite paragenesis systems.

DETAILED DESCRIPTION OF EMBODIMENTS

Figure 1:
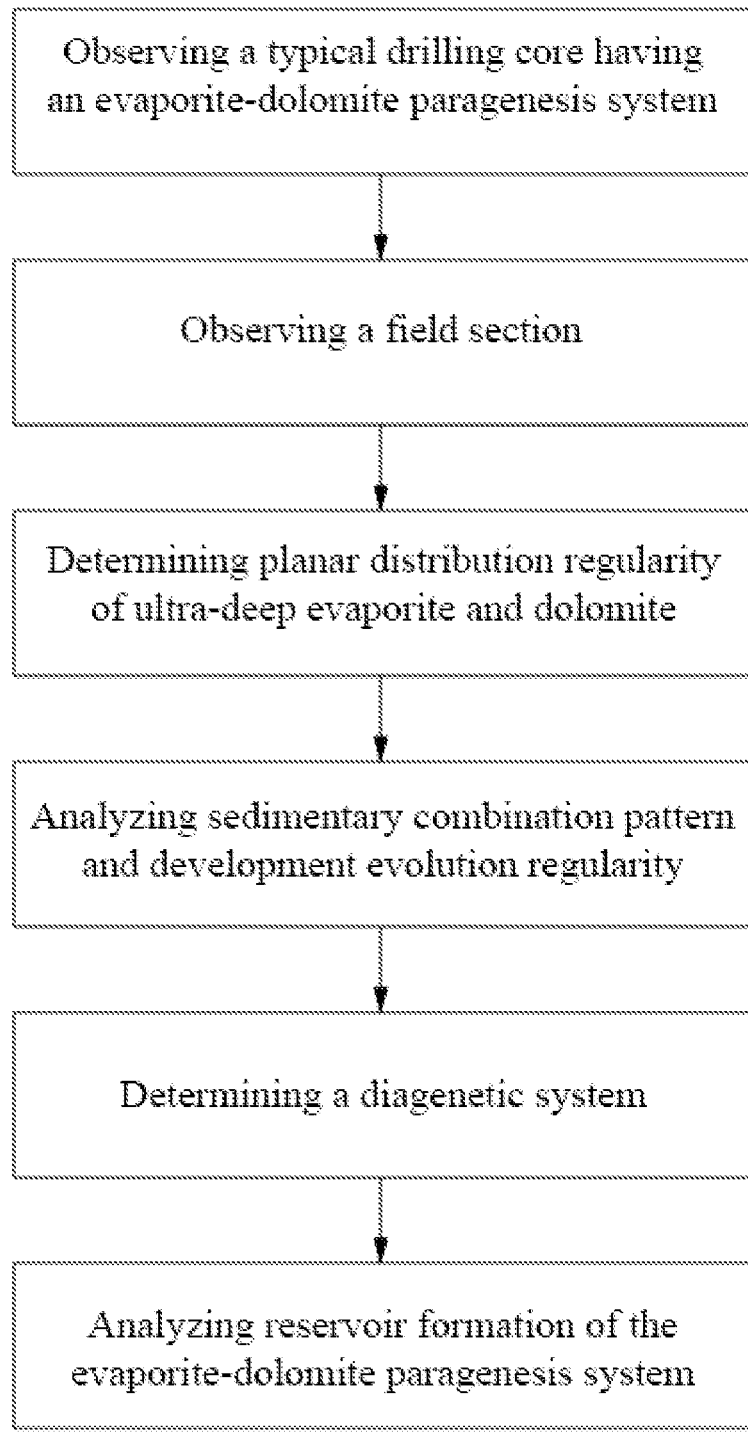
FIG. 1 is a flow chart of a method for quantitatively analyzing reservoir formation of an ultra-deep evaporite-dolomite paragenesis system in accordance with one embodiment of this application.

This application provides a method for quantitatively analyzing reservoir formation of an ultra-deep evaporite-dolomite paragenesis system. Considering that it is difficult to accurately trace diagenetic fluids and recover their characteristics, and the Sichuan Basin is characterized by multi-stage fluids and complex fluid activities, multiple advanced research methods are adopted to quantitatively analyze the formation mechanism of the diagenetic fluids between ultra-deep evaporite and dolomite. This application provides technical support for prediction, exploration and development of oil and gas reservoirs, especially the oil and gas reservoir of the Sichuan Basin.

The design idea of this application will be described as follows.

(1) Tracing of Characteristics, Stage and Migration Pattern of the Diagenetic Fluids of Ultra-Deep Evaporite-Dolomite Paragenesis System According to the logging analysis, core observation and field section measurement and observation in combination with thin section observation and cathode luminescence, development characteristics of the lithological combination of a development section of the paragenesis system are clarified to carry out the basic petrology and sedimentology research on this system. Moreover, the vertical combination pattern and development regularity of gypsum rock, salt rock and dolomite are systematically analyzed; the lithofacies combination type of the carbonate system containing evaporite is identified; and the type and characteristics of dolomite under different combination patterns are analyzed.

The analysis of nontraditional mental stable isotopes (predominated by Mg isotopes), and the laser-based in-situ micro-analysis of trace elements and isotopes are conducted in combination with the analysis of main trace elements and salt inclusions to clarify the type, origin, and the mineral and chemical composition of sedimentation-diagenesis fluids in this system. A novel high-accuracy isotopic dating technology (laser-based in-situ U—Pb dating of calcite) is adopted to reveal the time sequence of the fluid evolution and re-establish the fluid evolution process, so as to analyze the time sequences and coupling relationship between different types of fluids.

Combined with the numerical simulation of Mg isotopes, the origin, properties (such as temperature and pressure), and the migration pattern of dolomitized fluids are constrained. Different types of dolomitization processes are identified in the evaporite-bearing carbonate system, and the properties and evolution path of the sedimentation-diagenesis fluids as well as the tectonic dynamic of fluid activities from different stages are traced, so as to explore the evolution path and the reservoir formation of dolomitized fluids.

(2) Recovery and Simulation of Burial Temperature-Pressure Change History of Evaporite-Dolomite Paragenesis System Based on the research results of sedimentology, petrology and geochemistry, the lithological combination type, the type of the dissolution modified fluid and the control effect of different ions on the dissolution-precipitation equilibrium in a carbonate system containing evaporite are clarified. The mineral microscopic morphological characteristics such as crystal morphology, crystal size, crystal contact relationship, pore connectivity, etc., and changes of the reservoir space in the presence of different ions are quantitatively characterized. The CT (Computed Tomography) scanning of the reservoir space before and after reservoir corrosion is performed to enable the 3D characterization of the microporous structure, fracture distribution and microscopic seepage characteristics, so as to quantitatively analyze rock physical parameters. On the basis of geochemical tracing and "water-rock" interaction diagenesis simulation, combined with the analysis of fluid inclusions and clumped isotopes, and the burial history, temperature-pressure field and fluid field of the survey area are used to simulate different temperature-pressure conditions of the target stratum during the sedimentation-diagenesis process. The dissolution kinetics simulation experiment is conducted to clarify the role of different ions in the acidic media in controlling the dissolution kinetics reaction.

(3) Reservoir Formation in Sedimentation-Diagenesis Process of Evaporite-Containing Carbonate System The petrological and mineralogical characteristics of the reservoir development section are analyzed, and the petrologic fabric and substance composition of different types of reservoirs are clarified. Moreover, the dolomite reservoir type, reservoir space characteristics, physical properties and pore structure of paragenesis systems under different combinations are figured out. The reservoir development differences between paragenesis and non-paragenesis systems, as well as the physical characteristics, the reservoir space type and the reservoir space combination relationship of different types of reservoirs, are analyzed. Combined with the distribution and combination of metamorphic and authigenic minerals in carbonate reservoirs in fluid activity areas, flow processes of different types of fluids, as well as the modification process and scale of carbonate reservoirs caused by the fluids and the resulting water-rock interaction, are clarified. On this basis, the reservoir is divided according to the characteristics of the reservoir space development, the change extent and the fracture development. Combined with the tracing of properties, stages and migration patterns of diagenetic fluids, water-rock interaction and simulation experiments, the diagenetic-porosity evolution history is clarified, and different diagenetic evolution stages and the corresponding diagenetic environments are obtained. The diagenetic mechanism is determined, and the spatio-temporal coupling between the sedimentation diagenesis and reservoirs is explored. The diagenetic evolution model of the high-quality reservoirs during the sedimentation-diagenesis process of evaporite-containing carbonate systems is established, and the main factor controlling the development of high-quality reservoirs of the evaporite-containing carbonate system is determined.

Based on the above design principle, the technical solutions of this application will be further described below with reference to the embodiment.

Some instruments involved in this application are introduced as follows.

Polarized optical microscope (DM4500P) is used for observing dolomite microfabric and identifying mineral composition.

High resolution scanning electron microscope (SEM) is used for observing the ultramicroscopic morphology and structure of dolomite and evaporite minerals.

X-ray diffraction (XRD) is used for identifying the structure characteristics of dolomite and evaporite minerals, the order degree of dolomite and content changes of some elements (Fe, Mn, etc.) in different parts of crystals.

Electron probe microanalyzer (EPMA) is used for obtaining micro-area morphology images and the corresponding composition of a survey area, as well as the quantitative analysis of constituent elements.

Cathodoluminescence analysis (CL8200 Mk5-2 type cathodoluminescence microscope) is used to reflect classification of dolomite and evaporite minerals and microenvironmental changes in diagenetic fluids.

Inductively coupled plasma-mass spectrometer is used for exploration of diagenetic changes, palaeosedimentary environment, elemental migration rules, hydrothermal genesis identification, hydrothermal physico-chemical conditions, and characteristic identification.

C and O isotope analysis is used to analyze the paleoenvironment of dolomite, tracer carbon sources and determine the fluid properties and sources. A Finnigan MAT 253 IRMS isotope ratio mass spectrometer coupled to GasBench II, a TC/EA elemental analyzer and a gas chromatograph through Conflo IV can achieve the measurement of C and O isotopes.

THMSG-600 hot and cold stage system is used for the measurement of homogeneous temperature and salinity of fluid inclusions in dolomite.

Laser Raman analysis of fluid inclusions is used for the determination of composition of gas and fluid phases of fluid inclusions in dolomite. The THMSG-600 hot and cold stage system (produced by Linkam (UK)) equipped with a Renishaw inVia series (UK) new laser confocal microscopic Raman spectrometer can satisfy the sample analysis.

Referring to the flow chart shown in FIG. 1, the method provided herein mainly includes: observation of a typical drilling core containing an evaporite-dolomite paragenesis system, observation and measurement of a field section, determination of the planar distribution regularity of ultra-deep evaporite and dolomite, analysis of sedimentary combination patterns and development evolution regularity, determination of the diagenetic system and the analysis of the reservoir formation of the evaporite-dolomite paragenesis system.

Step (1) Observation of a Typical Drilling Core Containing an Evaporite-Dolomite Paragenesis System A typical key drilled well is selected for the observation of the core characteristics of a development section of the evaporite-dolomite paragenesis system, and the vertical development characteristics of the ultra-deep evaporite-dolomite paragenesis system are described and determined to determine the development and distribution regularity of the paragenesis system.

Step (2) Observation and Measurement of the Field Section

A typical field outcrop section is selected. The field outcrop data of the evaporite-dolomite paragenesis system is obtained through combination of typical section measurement and key section observation. A relevant sample is collected for laboratory research.

Step (3) Single-Factor Analysis of Logging Data and Determination of the Planar Distribution Regularity of the Ultra-Deep Evaporite and Dolomite The logging data of the evaporite stratum (e.g., the logging data of an evaporite stratum encountered in the Sichuan Basin) is systematically collected to establish a lithology identification plate. The thickness of the evaporite is recorded, and the planar boundary of the evaporite is marked. A thickness isoline map of the evaporite and the dolomite is established in a layered manner to identify the planar distribution regularity of individual components of the paragenesis system.

Step (4) Analysis of Sedimentary Combination Patterns and Development Evolution Regularity Based on the development and distribution regularity obtained in step (1) and the field outcrop data obtained in step (2), a combination pattern of the ultra-deep evaporite-dolomite paragenesis system is analyzed and determined to investigate an evolution pattern and a planar distribution characteristic of a combination of different substances in the ultra-deep evaporite-dolomite paragenesis system.

Step (5) Determination of the Diagenetic System

With a salt inclusion as an initial fluid, a property of a diagenetic fluid is inversed by measuring race and rare-earth elements, C, O, Sr and Mg isotopes and clumped isotopes of the dolomite. A simulation experiment of a water-rock interaction during a main evolution phase is performed according to petrological characteristics in combination with burial history. With formation water in a current drilled well as an end point, temperature and pressure characteristics and water-rock interaction process of a diagenetic system are systematically inversed to obtain characteristics of a diagenetic field and transformation force and evolution process of the diagenetic field, so as to determine the diagenetic system.

The accurate measurement of Mg isotopes in dolomite is a key point in this application. The analysis and measurement of Mg isotopes mainly involves the separation and purification of Mg and determination of the isotope ratio. Based on petrographic section analysis, the micro-area sampling is performed according to carbonate composition. A powder sample is dissolved with a 0.5 n acetic acid solution, Mg is purified from the sample solution with an ion exchange column. Finally, the Mg isotope ratio is measured by using a MC-ICP-MS (Multi-Collector-Inductively Coupled Plasma-Mass Spectrometer), with a measurement accuracy reaching 0.1‰.

Step (6) Analysis of the Reservoir Formation of the Evaporite-Dolomite Paragenesis System Based on the planar distribution pattern obtained in step (3) and the evolution pattern and the planar distribution characteristic obtained in step (4), a type of a reservoir is identified, and development characteristic and regularity of the reservoir are analyzed. Based on the diagenetic system determined in step (5), an evolution process and a formation mechanism of the reservoir are analyzed to establish a reservoir development model. The reservoir formation of the ultra-deep evaporite-dolomite paragenesis system is quantitatively analyzed based on the reservoir development model.

Figure 2:
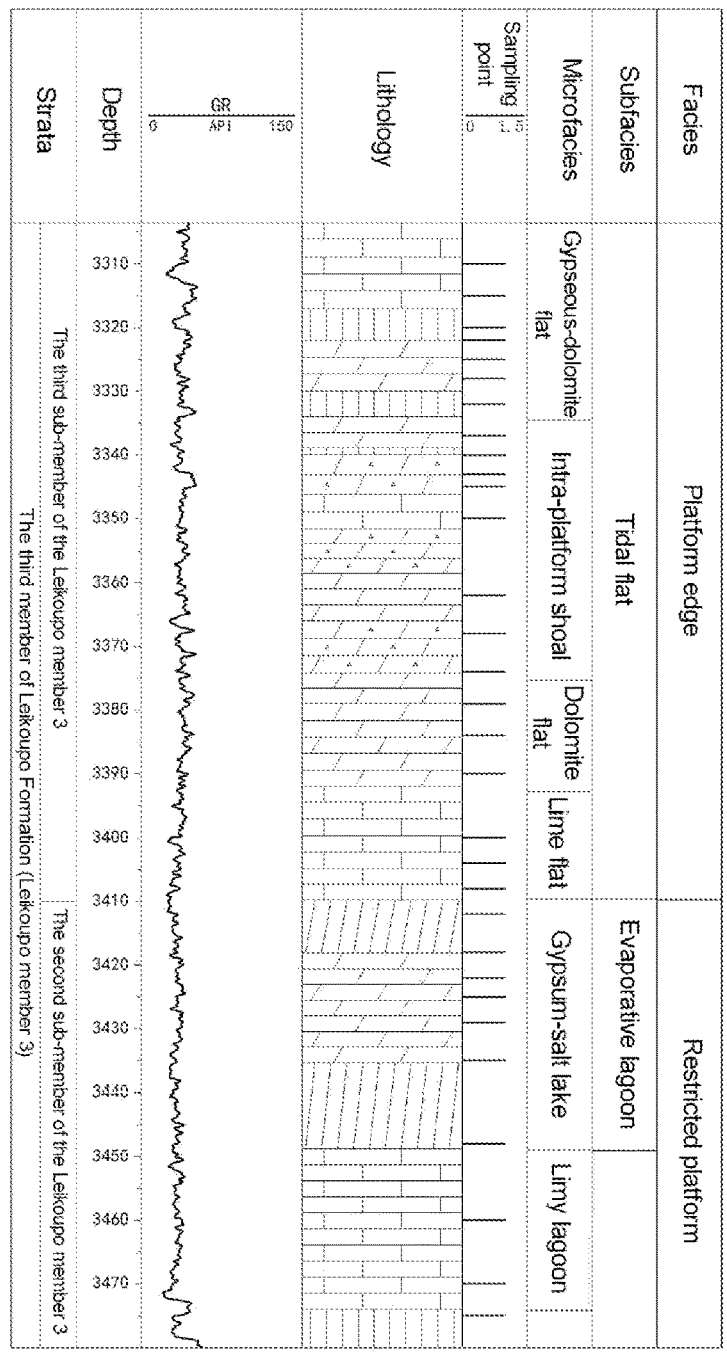
FIG. 2 schematically shows formation mechanism of the diagenetic fluid between ultra-deep evaporite and dolomite in accordance with one embodiment this application.
Figure 2:
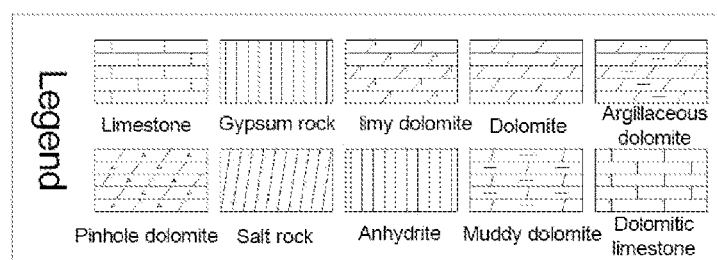

This application selects the Leikoupo Formation in the Sichuan Basin as an example for the exploration of reservoir formation of ultra-deep evaporite-dolomite paragenesis systems. Since there are multi-stage fluids and complex fluid activities in the Sichuan Basin, the diagenesis of the paragenesis systems is classified into dolomitization, dedolomitization, dissolution, compaction and pressure dissolution, and the characteristics and migration path of the diagenetic fluid in paragenesis systems are qualitatively analyzed to recover the formation mode of paragenesis systems, so as to quantitatively analyze the formation mechanism of the diagenetic fluid between ultra-deep evaporite and dolomite, which is shown in FIG. 2.

This application quantitatively analyzes the development differences and similarities between the paragenesis and non-paragenesis systems, and according to petrology, sedimentology and sedimentary geochemistry research results, the development and spatial distribution characteristics of the lithofacies assemblage pattern in evaporite-dolomite paragenesis system are determined, thereby providing reliable support for the prediction, exploration and development of oil and gas reservoirs in the Sichuan Basin.

Described above are merely preferred embodiments of this application, and are not intended to limit the scope of this application. It should be understood that any variations, modifications and replacements made by those skilled in the art without departing from the spirit of the disclosure shall fall within the scope of the disclosure defined by the appended claims.

What is claimed is:

1. A method for quantitatively analyzing reservoir formation of an ultra-deep evaporite-dolomite paragenesis system, comprising:

step (1) selecting a typical key drilled well to observe a core characteristic of a development section of the ultra-deep evaporite-dolomite paragenesis system; and describing and determining a vertical development characteristic of the ultra-deep evaporite-dolomite paragenesis system to determine a development and distribution regularity of the ultra-deep evaporite-dolomite paragenesis system;

step (2) selecting a typical field outcrop section; obtaining field outcrop data of the ultra-deep evaporite-dolomite paragenesis system through combination of typical section measurement and key section observation; and collecting a paragenetic evaporite-dolomite sample for laboratory research;

step (3) systematically collecting logging data of an evaporite stratum to establish a lithology identification plate; recording a thickness of an evaporite and marking a planar boundary of the evaporite; establishing a thickness isoline map of the evaporite and a dolomite in a layered manner; and identifying a planar distribution pattern of individual components of the ultra-deep evaporite-dolomite paragenesis system;

step (4) based on the development and distribution regularity obtained in step (1) and the field outcrop data obtained in step (2), analyzing and determining a combination pattern of the ultra-deep evaporite-dolomite paragenesis system to investigate an evolution pattern and a planar distribution characteristic of a combination of different substances in the ultra-deep evaporite-dolomite paragenesis system;

step (5) with a salt inclusion as an initial fluid, inversing a property of a diagenetic fluid by measuring race and rare-earth elements, C, O, Sr and Mg isotopes and clumped isotopes of the dolomite; performing a simulation experiment of a water-rock interaction during a main evolution phase according to petrological characteristics of the ultra-deep evaporite-dolomite paragenesis system in combination with burial history; and with strata water in a current drilled well as an end point, systematically inversing temperature and pressure characteristics and water-rock interaction process of a diagenetic system to obtain characteristics of a diagenetic field and a transformation force and an evolution process of the diagenetic field, so as to determine the diagenetic system; and step (6) based on the planar distribution pattern obtained in step (3) and the evolution pattern and the planar distribution characteristic obtained in step (4), identifying a type of a reservoir, and analyzing development characteristic and regularity of the reservoir;

based on the diagenetic system determined in step (5), analyzing an evolution and formation process of the reservoir and a reservoir formation mechanism to establish a reservoir development model; and quantitatively analyzing the reservoir formation of the ultra-deep evaporite-dolomite paragenesis system based on the reservoir development model.

2. The method of claim 1, wherein in step (5), Mg isotope is measured through steps of:

(a) based on petrographic section analysis, performing micro-area sampling according to carbonate composition;

(b) dissolving a powder sample with a 0.5 N acetic acid solution to obtain a sample solution;

(c) purifying Mg from the sample solution with an ion exchange column; and (d) measuring a Mg isotope ratio by using a Multi-Collector Inductively Coupled Plasma-Mass Spectrometry (MC-ICP-MS) solution method.

3. The method of claim 2, wherein microstructure observation and mineral composition identification of the dolomite are performed by using a polarized optical microscope.

4. The method of claim 3, wherein ultramicroscopic mineral morphology and structure of the evaporite and the dolomite are observed under a scanning electron microscope (SEM).

5. The method of claim 4, wherein mineral structure characteristics of the evaporite and dolomite, variation of an order degree of the dolomite and variation of Fe and Mn in crystals of the dolomite are identified by X-ray diffraction (XRD).

6. The method of claim 5, wherein obtaining of a micro-area morphological image of a survey area and quantitative analysis of components and constituent elements of the survey area are performed by using an electron probe microanalyzer (EPMA).

7. The method of claim 6, wherein mineral classification of the evaporite and dolomite and a microenvironmental change of the diagenetic fluid are analyzed by cathodoluminescence (CL).

* * * * *